US006211209B1

(12) United States Patent
Baragi et al.

(10) Patent No.: US 6,211,209 B1
(45) Date of Patent: *Apr. 3, 2001

(54) METHOD OF INHIBITING CONNECTIVE TISSUE DEGRADATION

(75) Inventors: Vijaykumar Baragi, Ann Arbor, MI (US); Diane Harris Boschelli, New City, NY (US); David Thomas Connor, Ann Harbor; Richard Raymond Renkiewicz, Novi, both of MI (US); Howard Glenn Welgus, Chesterfield, MO (US)

(73) Assignee: Warner-Lambert Company, Morris Plains, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/130,215

(22) Filed: Aug. 6, 1998

Related U.S. Application Data
(60) Provisional application No. 60/055,172, filed on Aug. 8, 1997.

(51) Int. Cl.$^7$ .................................................. A61K 31/41
(52) U.S. Cl. .......................... 514/361; 514/363; 514/364; 514/384
(58) Field of Search .................................... 514/361, 384, 514/363, 364, 385

(56) References Cited

U.S. PATENT DOCUMENTS

| | | | |
|---|---|---|---|
| 3,531,493 | 9/1970 | Gittos et al. | 514/363 |
| 4,962,119 | 10/1990 | Boschelli et al. | 514/384 |
| 5,066,668 | 11/1991 | Boschelli et al. | 514/384 |
| 5,114,958 | 5/1992 | Boschelli et al. | 514/361 |
| 5,143,929 | 9/1992 | Belliotti et al. | 514/364 |
| 5,212,189 | 5/1993 | Belliotti et al. | 514/363 |
| 5,358,964 | 10/1994 | Baragi et al. | 514/471 |
| 5,677,282 | * 10/1997 | Oleksyszyn et al. | 514/118 |
| 5,847,148 | * 12/1998 | Jacobsen et al. | 548/140 |
| 5,902,791 | * 5/1999 | Beckett et al. | 514/19 |

OTHER PUBLICATIONS

Woessner, Jr., "Matrix metalloprotieinases and their inhibitors in connective tissue remodeling", The FASEB Journal, 1991, vol. 5, pp. 2145–2154.

Ranst, et al., "The Cytokine–Protease Connection: Identification of a 96–kD THP–1 Gelatinase and Regulation by Interkeukin–1 and Cytokine Inducers", Cytokine, 1991, vol. 3, No. 3, pp. 231–239.

Unemori, et al., "Constitutive Expression of a 92–kD Gelatinase (Type V Collagenase) by Rheumatoid Synovial Fibroblasts and Its Induction in Normal Human Fibroblasts by Inflammatory Cytokines", J. Clin. Invest., 1991, vol. 88, pp. 1656–1662.

K.D. Rainsford, "Effects of Meloxicam, Compared with other NS AIDs, on Cartilage Proteoglycan Metabolism, Synovial Prostaglandin $E_2$, and Production of Interleukins 1, 6 and 8, in Human and Porcine Explants in Organ Culture," J. Pharm. Pharmacol., 1997, pp. 991–998.

E.C. Arner et al., "Independent Effects of Interleukin–1 on Proteoglycan Breakdown, Proteoglycan Synthesis, and Prostaglandin $E_2$ Release From Cartilage in Organ Culture," Arthritis and Rheumatism, vol. 32, No. 3, Mar. 1989, pp. 288–297.

E.C. Arner et al., "Effect of Antiinflammatory Drugs on Human Interleukin–1–Induced Cartilage Degradation," Agents and Actions, vol. 21, 3/4, 1987, pp. 334–336.

J. Steinmeyer et al., "Pharmacological Influence of Antirheumatic Drugs on Proteoglycanases from Interleukin–1 Treated Articular Cartilage," Bichemical Pharmacology, vol. 53, 1997, pp. 1627–1635.

M.J. Palmoski et al., "Effects of Some Nonsteroidal Antiinflammatory Drugs on Proteoglycan Metabolism and Organization in Canine Articular Cartilage," Arthritis and Rheumatism, vol. 23, No. 9, Sep. 1980, pp. 1010–1020.

M. Doherty et al., Editorial, "Indomethacin Hastens Large Joint Osteoarthritis in Humans—How Strong is the Evidence," The Journal of Rheumatology, 1995, pp. 2013–2015.

J.H. Herman et al., "The In vitro Effect of Select Classes of Nonsteroidal Antiinflammatory Drugs on Normal Cartilage Metabolism," The Journal of Rheumatology, 1986, pp. 1014–1018.

\* cited by examiner

Primary Examiner—James H. Reamer
(74) Attorney, Agent, or Firm—Charles W. Ashbrook

(57) ABSTRACT

The present invention provides a method of inhibiting connective tissue degradation that comprises administering to a patient having a condition in which connective tissue is degraded a therapeutically effective amount of a compound having the formula

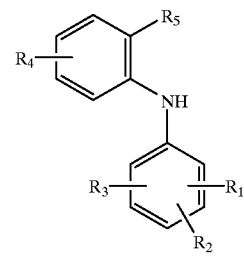

where $R_1$, $R_2$, $R_3$, and $R_4$ are independently hydrogen, hydroxy, halo, amino, nitro, $C_1$–$C_6$ alkyl, $C_3$–$C_6$ cycloalkyl, $C_1$–$C_6$ alkoxy, $CF_3$, CN, $S(O)_n$—, $R_6$ and $R_7$ are independently hydrogen, $C_1$–$C_6$ alkyl, or acyl;

n is 0 to 2;

$R_8$ is hydrogen or $C_1$–$C_6$ alkyl;

A is 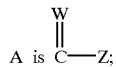

W is S or O;

Z is $C_1$–$C_6$ alkyl, $C_1$–$C_6$ alkoxy, or $NR_9R_{10}$;

$R_9$ and $R_{10}$ are independently hydrogen or $C_1$–$C_6$ alkyl; and $R_5$ is

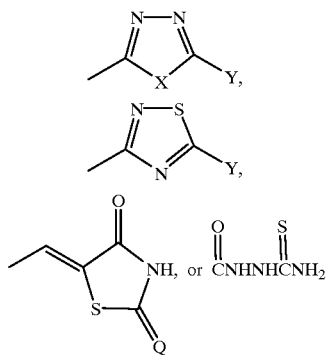

where Y is hydroxy, thiol, amino, or NHCN;

X is sulfur or oxygen; and Q is sulfur, oxygen, NH, or NCN, and the pharmaceutically acceptable salts and prodrugs thereof. Also provided is a method of inhibiting the production of matrix metalloproteinases comprising administering to a patient having a condition associated with matrix metalloproteinase-mediated tissue degradation a therapeutically effective amount of a compound having the formula

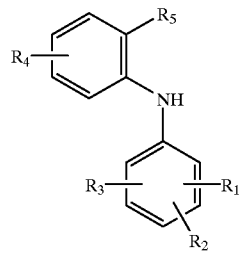

where $R_1$, $R_2$, $R_3$, and $R_4$ are independently hydrogen, hydroxy, halo, amino, nitro, $C_1$–$C_6$ alkyl, $C_3$–$C_6$ cycloalkyl, $C_1$–$C_6$ alkoxy, $CF_3$, CN, $S(O)_n$—,

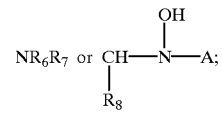

$R_6$ and $R_7$ are independently hydrogen, $C_1$–$C_6$ alkyl or acyl;

n is 0 to 2;

$R_8$ is hydrogen or $C_1$–$C_6$ alkyl;

A is 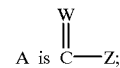

W is S or O;

Z is $C_1$–$C_6$ alkyl, $C_1$–$C_6$ alkoxy, or $NR_9R_{10}$;

$R_9$ and $R_{10}$ are independently hydrogen or $C_1$–$C_6$ alkyl; and $R_5$ is

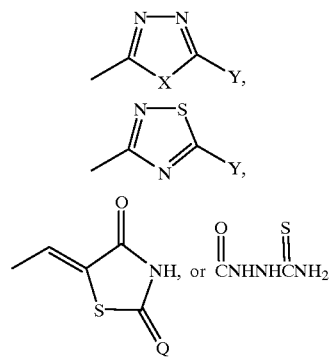

where Y is hydroxy, thiol, amino, or NHCN;

X is sulfur or oxygen; and Q is sulfur, oxygen, NH, or NCN, and the pharmaceutically acceptable salts and prodrugs thereof.

44 Claims, 1 Drawing Sheet

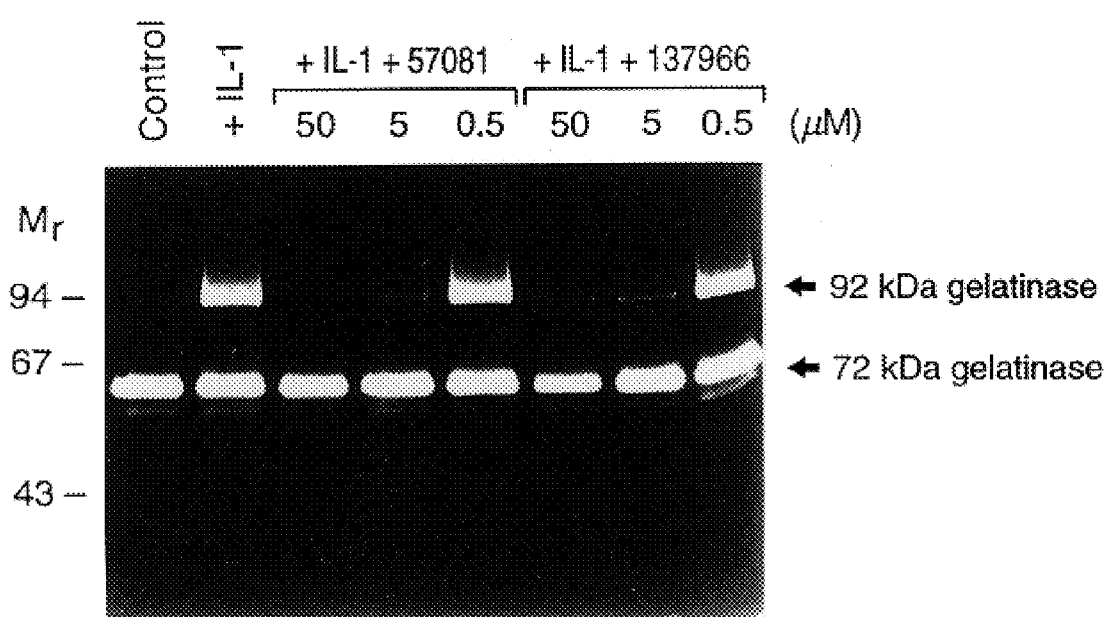

METHOD OF INHIBITING CONNECTIVE TISSUE DEGRADATION

A CROSS REFERENCE TO RELATED APPLICATION

This application claims priority of U.S. Ser. No. 60/055,172 filed on Aug. 8, 1997.

FIELD OF THE INVENTION

This invention relates to a method of inhibiting connective tissue degradation. This invention also relates to a method of inhibiting the production of matrix metalloproteinases.

BACKGROUND OF THE INVENTION

In certain conditions, connective tissues in a patient are detrimentally degraded. For example, cartilage can be degraded as a result of a disease, or injury from a mechanical trauma, such as a sports accident; the bones or intervertebral disks of a patient can be degraded due to various environmental conditions or diseases; dermis of the skin can be degraded in the elderly causing chronic ulcers; and degradation of the connective tissue of blood vessels can lead to aneurysm formation or atherosclerosis. The term "connective tissue" means the structural framework of organs containing supporting matrix molecules such as collagens, elastins, and proteoglycans (glycosaminogylcans).

In conditions in which connective tissue degradation occurs, matrix metalloproteinases are known to play an important role in the degradation of the tissues. A good review of the matrix metalloproteinases and their role in tissue degradation can be found in the article "Matrix Metalloproteinases and Their Inhibitors In Connective Tissue Remodelling" by J. Frederick Woessner, Jr., *The FASEB Journal*, 1991;5:2145–2154.

Presently, there is no way of inhibiting the tissue degradation that results from such conditions, and physicians have, instead, prescribed compounds that act to mask the symptoms, i.e., ameliorate the pain associated with such conditions, but these compounds have not inhibited the tissue degradation. That is, destruction of the tissues continues unabated despite symptomatic relief. Eventually, the tissues are destroyed by the disease process and dysfunction occurs.

Thus, it would be beneficial to have a method to inhibit connective tissue degradation in a patient.

SUMMARY OF THE INVENTION

The present invention provides a method of inhibiting connective tissue degradation that comprises administering to a patient having a condition in which connective tissue is degraded a therapeutically effective amount of a compound having the formula where $R_1$, $R_2$, $R_3$, and $R_4$ are independently hydrogen, hydroxy, halo, amino, nitro, $C_1$–$C_6$ alkyl, $C_3$–$C_6$ cycloalkyl, $C_1$–$C_6$ alkoxy, $CF_3$, CN, $S(O)_n$—[$C_1$–$C_6$ alkyl], $$NR_6R_7 \text{ or } \underset{R_8}{\overset{OH}{\underset{|}{CH}}}-\overset{|}{N}-A;$$

$R_6$ and $R_7$ are independently hydrogen, $C_1$–$C_6$ alkyl or acyl;

n is 0 to 2;

$R_8$ is hydrogen or $C_1$–$C_6$ alkyl;

$$A \text{ is } \overset{W}{\underset{\|}{C}}-Z;$$

W is S or O;

Z is $C_1$–$C_6$ alkyl, $C_1$–$C_6$ alkoxy or $NR_9R_{10}$;

$R_9$ and $R_{10}$ are independently hydrogen or $C_1$–$C_6$ alkyl; and $R_5$ is where Y is hydroxy, thiol, amino or NHCN;

X is sulfur or oxygen; and Q is sulfur, oxygen, NH or NCN, and the pharmaceutically acceptable salts and prodrugs thereof.

In one embodiment of the invention, $R_5$ is

In another embodiment of the invention, $R_5$ is

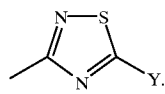

In a third embodiment of the invention, $R_5$ is

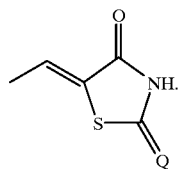

In another embodiment of the invention, $R_5$ is

Also provided is a method of inhibiting the production of matrix metalloproteinases comprising administering to a patient having a condition associated with matrix metalloproteinase-mediated tissue degradation a therapeutically effective amount of a compound having the formula

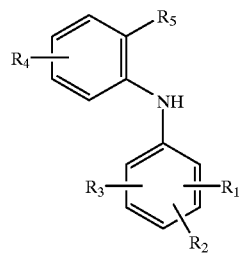

where $R_1$, $R_2$, $R_3$, and $R_4$ are independently hydrogen, hydroxy, halo, amino, nitro, $C_1$–$C_6$ alkyl, $C_3$–$C_6$ cycloalkyl, $C_1$–$C_6$ alkoxy, $CF_3$, CN, $S(O)_n$—[$C_1$–$C_6$ alkyl],

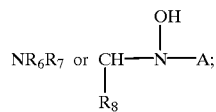

$R_6$ and $R_7$ are independently hydrogen, $C_1$–$C_6$ alkyl or acyl;
n is 0 to 2;
$R_8$ is hydrogen or $C_1$–$C_6$ alkyl;

W is S or O;
Z is $C_1$–$C_6$ alkyl, $C_1$–$C_6$ alkoxy or $NR_9R_{10}$;
$R_9$ and $R_{10}$ are independently hydrogen or $C_1$–$C_6$ alkyl; and $R_5$ is

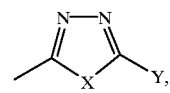

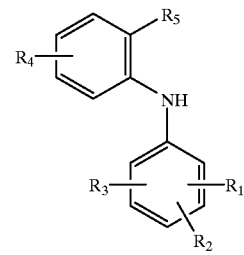

where Y is hydroxy, thiol, amino or NHCN; X is sulfur or oxygen; and Q is sulfur, oxygen, NH or NCN, and the pharmaceutically acceptable salts and prodrugs thereof.

BRIEF DESCRIPTION OF THE DRAWING

FIG. 1 is a gelatin zymogram that shows the effect of two compounds of the present method on expression of 72 and 92 KDa gelatinases.

DETAILED DESCRIPTION OF THE INVENTION

The present invention provides a method of inhibiting connective tissue degradation, the method comprising administering to a patient having a condition in which connective tissue is degraded a therapeutically effective amount of a compound having the formula

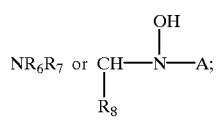

where $R_1$, $R_2$, $R_3$, and $R_4$ are independently hydrogen, hydroxy, halo, amino, nitro, $C_1$–$C_6$ alkyl, $C_1$–$C_6$ cycloalkyl, $C_1$–$C_6$ alkoxy, $CF_3$, CN, $S(O)_n$—[$C_1$–$C_6$ alkyl], $$NR_6R_7 \text{ or } \underset{R_8}{CH}-\overset{OH}{N}-A;$$

$R_6$ and $R_7$ are independently hydrogen, $C_1$–$C_6$ alkyl or acyl;
n is 0 to 2;

$R_8$ is hydrogen or $C_1$–$C_6$ alkyl;

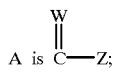

W is S or O;
Z is $C_1$–$C_6$ alkyl, $C_1$–$C_6$ alkoxy or $NR_9R_{10}$;
$R_9$ and $R_{10}$ are independently hydrogen or $C_1$–$C_6$ alkyl; and $R_5$ is

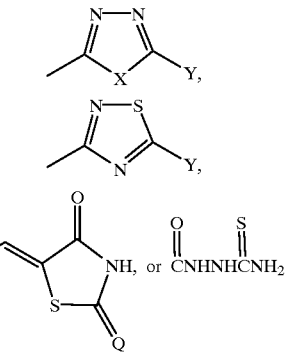

where Y is hydroxy, thiol, amino or NHCN;
X is sulfur or oxygen; and Q is sulfur, oxygen, NH or NCN, and the pharmaceutically acceptable salts and prodrugs thereof.

In one embodiment of the method, $R_5$ is

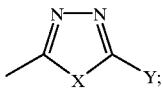

$R_4$ is hydrogen; $R_1$, $R_2$, and $R_3$ are independently hydrogen, hydroxy, halo, amino, nitro, $C_1$–$C_6$ alkyl, $C_1$–$C_6$ cycloalkyl, $C_1$–$C_6$ alkoxy, $CF_3$, or CN; and Y is hydroxy, thiol, amino, or NHCN.

In another embodiment of the method, $R_5$ is

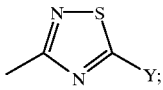

$R_4$ is hydrogen; $R_1$, $R_2$, and $R_3$ are independently hydrogen, hydroxy, halo, amino, nitro, $C_1$–$C_6$ alkyl, $C_1$–$C_6$ cycloalkyl, $C_1$–$C_6$ alkoxy, $CF_3$, or CN; and Y is hydroxy, thiol, amino, or NHCN.

In a third embodiment of the method, $R_5$ is

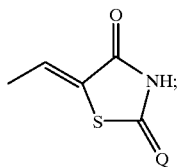

$R_4$ is hydrogen; $R_1$, $R_2$, and $R_3$ are independently hydrogen, hydroxy, halo, amino, nitro, $C_1$–$C_6$ alkyl, $C_1$–$C_6$ cycloalkyl, $C_1$–$C_6$ alkoxy, $CF_3$, or CN; and Q is sulfur, oxygen, NH, or NCN.

In a fourth embodiment of the method $R_5$ is

$R_4$ is hydrogen; and $R_1$, $R_2$, and $R_3$ are independently hydrogen, hydroxy, halo, amino, nitro, $C_1$–$C_6$ alkyl, $C_1$–$C_6$ cycloalkyl, $C_1$–$C_6$ alkoxy, $CF_3$, or CN.

In another preferred embodiment of the invention, $R_1$ is

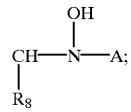

$R_4$ is hydrogen; $R_2$ and $R_3$ are independently hydrogen, hydroxy, halo, amino, nitro, $C_1$–$C_6$ alkyl, $C_1$–$C_6$ cycloalkyl, $C_1$–$C_6$ alkoxy, $CF_3$, or CN;
$R_5$ is

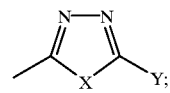

X is sulfur or oxygen; and
Y is hydroxy, thiol, amino, or NHCN.

The present invention also provides a method of inhibiting the production of matrix metalloproteinases, the method comprising administering to a patient having a condition associated with matrix metalloproteinase-mediated tissue degradation a therapeutically effective amount of a compound having the formula

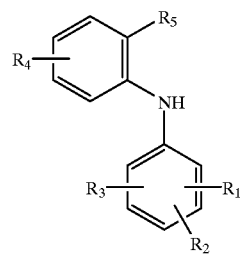

where $R_1$, $R_2$, $R_3$, and $R_4$ are independently hydrogen, hydroxy, halo, amino, nitro, $C_1$–$C_6$ alkyl, $C_3$–$C_6$ cycloalkyl, $C_1$–$C_6$ alkoxy, $CF_3$, CN, $S(O)_n$—[$C_1$–$C_6$ alkyl],

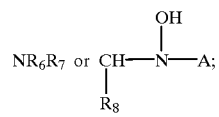

$R_6$ and $R_7$ are independently hydrogen, $C_1$–$C_6$ alkyl or acyl;

n is 0 to 2;

$R_8$ is hydrogen or $C_1$–$C_6$ alkyl;

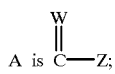

W is S or O;
Z is $C_1$–$C_6$ alkyl, $C_1$–$C_6$ alkoxy, or $NR_9R_{10}$;
$R_9$ and $R_{10}$ are independently hydrogen or $C_1$–$C_6$ alkyl; and $R_5$ is

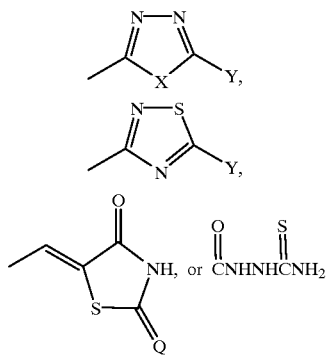

where Y is hydroxy, thiol, amino, or NHCN;
X is sulfur or oxygen; and Q is sulfur, oxygen, NH, or NCN, and the pharmaceutically acceptable salts and prodrugs thereof.

In one embodiment, $R_5$ is

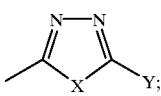

$R_4$ is hydrogen; $R_1$, $R_2$, and $R_3$ are independently hydrogen, hydroxy, halo, amino, nitro, $C_1$–$C_6$ alkyl, $C_1$–$C_6$ alkoxy, $CF_3$, or CN; and Y is hydroxy, thiol, amino, or NHCN.

In another embodiment, $R_5$ is

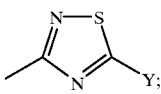

$R_4$ is hydrogen; $R_1$, $R_2$, and $R_3$ are independently hydrogen, hydroxy, halo, amino, nitro, $C_1$–$C_6$ alkyl, $C_1$–$C_6$ alkoxy, $CF_3$ or CN; and Y is hydroxy, thiol, amino, or NHCN.

In a third embodiment, $R_5$ is

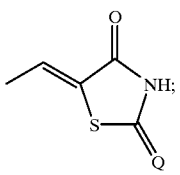

$R_4$ is hydrogen; $R_1$, $R_2$, and $R_3$ are independently hydrogen, hydroxy, halo, amino, nitro, $C_1$–$C_6$ alkyl, $C_1$–$C_6$ alkoxy, $CF_3$, or CN; and Q is sulfur, oxygen, NH, or NCN.

In a forth embodiment,

$R_4$ is hydrogen; and $R_1$, $R_2$ and $R_3$ are independently hydrogen, hydroxy, halo, amino, nitro, $C_1$–$C_6$ alkyl, $C_1$–$C_6$ alkoxy, $CF_3$, or CN.

In another embodiment,

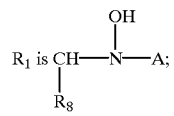

$R_4$ is hydrogen; $R_2$ and $R_3$ are independently hydrogen, hydroxy, halo, amino, nitro, $C_1$–$C_6$ alkyl, $C_1$–$C_6$ alkoxy, $CF_3$, or CN;
$R_5$ is

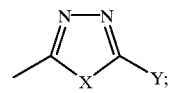

X is sulfur or oxygen; and
Y is hydroxy, thiol, amino, or NHCN.

The compounds of the present method inhibit the degradation of tissue in a patient. The compounds of the present method are also chondroprotective agents. That is, they inhibit the cartilage degradation mediated by chondrocytes, which are cells that are an essential part of cartilage.

The term "patient" means an animal, including a human. Representative examples of patients are humans, dogs, cats, rabbits, cows, horses, goats, sheep, and pigs.

The phrase inhibiting connective tissue degradation shall mean that the rate of degradation of connective tissue is less upon administration of a compound of the present method than the rate of degradation of connective tissue in the absence of the compound.

In general, the compounds of the present method are administered to a patient having a condition in which connective tissue is degrading or degraded. Such conditions include, but are not limited to, injury to cartilage, cancer, periodontal disease, multiple sclerosis, aneurysm formation, cutaneous and gastrointestinal ulcer formation, emphysema, atherosclerosis, and osteoporosis.

Examples of connective tissue include, but are not limited to, eye connective tissue (cornea), gastrointestinal connective tissue, neural interstitium, lung connective tissue, blood vessel matrix, periodontal tissue, dermis, bone, and cartilage.

The term "halo" means a halogen such as fluorine, chlorine, bromine, or iodine.

The term "$C_1$–$C_6$ alkyl" means an alkyl radical, including a straight chain or branched radical, having from 1 to 6 carbon atoms. Representative examples of $C_1$–$C_6$ alkyl radicals include methyl, ethyl, n-propyl, isopropyl, n-butyl, isobutyl, tert-butyl, pentyl, and hexyl.

The term "$C_3$–$C_6$ cycloalkyl" means an alkyl group that forms a ring structure. Representative examples of $C_3$–$C_6$ cycloalkyl radicals include cyclopropyl, cyclobutyl, cyclopentyl, and cyclohexyl.

The term "$C_1$–$C_6$ alkoxy" means a $C_1$–$C_6$ alkyl radical bonded to an oxygen atom. Representative examples of $C_1$–$C_6$ alkoxy radicals include methoxy, ethoxy, propoxy, isopropoxy, n-butoxy, tert-butoxy, pentoxy, and hexoxy.

The compounds of the present method have an inhibitory effect on the production of matrix metalloproteinases such as 92 kDa gelatinase, which is a metalloproteinase that plays a role in cartilage degradation. 92 kDa Gelatinase has also been indicated as playing a role in other conditions characterized by aberrant tissue destruction. Such conditions include cancer, multiple sclerosis, bone resorption, aneurysm formation, cutaneous ulcers, emphysema, atherosclerosis, and periodontal disease, all which can be treated using the compounds of the present method.

The phrase "therapeutically effective amount" means an amount of a compound of the present method, which when administered to a patient, inhibits the degradation of connective tissue and/or inhibits the production of matrix metalloproteinases in a patient.

The compounds of the present invention can be administered to a patient at dosage levels in the range of about 0.1 μg/kg body weight to about 500 mg/kg body weight per day. The specific dosage used, however, can vary. For example, the dosage can depend on a numbers of factors including the requirements of the patient, the severity of the condition being treated, and the pharmacological activity of the compound being used. The determination of optimum dosages for a particular patient is well known to those skilled in the art.

It is also contemplated that more than one compound of the present invention can be administered to a patient.

The compounds of the present invention can be administered to humans and animals either orally, rectally, parenterally (intravenously, intramuscularly, or subcutaneously), intracisternally, intravaginally, intraperitoneally, intravesically, locally (powders, ointments, or drops), or as buccal or nasal sprays.

Compositions that contain a compound of the present invention that are suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

The compositions may also contain adjuvants such as preserving, wetting, emulsifying and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars and sodium chloride and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is typically admixed with at least one inert excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (e) solution retarders, as for example, paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols and the like.

Solid dosage forms such as tablets, dragees, capsules, pills, and granules can be prepared with coatings and shells, such as enteric coatings and others well known in the art. They may contain opacifying agents and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the pharmacologically active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, compositions containing the present compounds can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administration are preferably suppositories which can be prepared by mixing the compounds of the present invention with suitable nonirritating excipients or carriers such as cocoa butter, polyethyleneglycol or a suppository wax, which are solid at ordinary temperatures but liquid at body temperature and therefore, melt in the rectum or vaginal cavity and release the active compounds.

Dosage forms for topical administration of a compound of this invention include ointments, creams, powders, sprays and inhalants. The active component is admixed under sterile conditions with a physiologically acceptable carrier and any preservatives, buffers or propellants as may be required. Ophthalmic formulations, eye ointments, powders, and solutions are also contemplated as being within the scope of this invention.

The compounds of the present invention can exist in different stereoisometric forms by virtue of the presence of asymmetric centers in the compounds. It is contemplated that all stereoisometric forms of the compounds as well as mixtures thereof, including racemic mixtures, form part of this invention.

The compounds of the present invention can also exist in different tautomeric forms. It is contemplated that all tautomeric forms as well as mixtures thereof, form part of this invention.

In addition, the compounds of the present invention can exist in unsolvated as well as solvated forms with pharmaceutically acceptable solvents such as water, ethanol and the like. In general, the solvated forms are considered equivalent to the unsolvated forms for the purposes of the present invention.

The term "pharmaceutically acceptable salts and prodrugs" as used herein refers to those carboxylate salts, amino acid addition salts, and prodrugs of the compounds of the present invention which are, within the scope of sound medical judgement, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively nontoxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactiobionate and laurylsulphonate salts, and the like. These may include cations based on the alkali and alkaline earth metals, such as sodium, lithium, potassium, calcium, magnesium, and the like, as well as nontoxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," *J. Pharm. Sci.*, 1977;66:1–19 which is incorporated herein by reference.) The term "prodrug" refers to compounds that are rapidly transformed in vivo to yield the parent compound of the above formulas, for example, by hydrolysis in blood. A thorough discussion is provided in T. Higuchi and V. Stella, "Pro-drugs as Novel Delivery Systems," Vol. 14 of the ACS Symposium Series, and in *Bioreversible Carriers in Drug Design*, ed. Edward B. Roche, American Pharmaceutical Association and Pergamon Press, 1987, both of which are incorporated herein by reference.

In addition to the compounds of the present method, pharmaceutical compositions can also contain other active ingredients, such as nonsteroidal antiinflammatory drugs (NSAIDS). The weight ratio of the compound of the present method to the second active ingredient may be varied and will depend upon the effective dose of each ingredient. Thus, for example, when a compound of the present method is combined with an NSAID, the weight ratio of the compound of the present method to the NSAID will generally range from about 1000:1 to about 1:1000, preferably about 200:1 to about 1:200.

It is also recognized that compounds of the present method and NSAIDS (or other active compounds) can be administered concurrently or separately. For example, two tablets can be administered at the same time, each tablet having a different active compound. On the other hand, two tablets having different active compounds can be administered at different times. It is also contemplated that more than one active compound can be administered to a patient in the same dosage form. For example, a compound of the present method and a NSAID may be administered together in the dosage form of a tablet.

NSAIDS can be characterized into five groups:

(1) the propionic acid derivatives;

(2) the acetic acid derivatives;

(3) the fenamic acid derivatives;

(4) the biphenylcarboxylic acid derivatives; and (5) the oxicams or a pharmaceutically acceptable salt thereof.

The propionic acid derivatives which may be used comprise: ibuprofen, ibuprofen aluminum, indoprofen, ketoprofen, naproxen, benoxaprofen, flurbiprofen, fenoprofen, fenbufen, pirprofen, carprofen, oxaprozin, pranoprofen, microprofen, tioxaprofen, suprofen, alminoprofen, tiaprofen, fluprofen, and bucloxic acid. Structurally related propionic acid derivatives having similar analgesic and antiinflammatory properties are also intended to be included in this group.

Thus, "propionic acid derivatives" as defined herein are nonnarcotic analgesics/nonsteroidal antiinflammatory drugs having a free —$CH(CH_3)COOH$ or —$CH_2CH_2COOH$ group (which optionally can be in the form of a pharmaceutically acceptable salt group, e.g., —$CH(CH_3)COO^-Na^+$ or —$CH_2(CH_2)COO^-Na^+$), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acematacin, fentiazac, clindanac, oxpinac, and fenclozic acid. Structurally related acetic acid derivatives having similar analgesic and antiinflammatory properties are also intended to be encompassed by this group.

Thus, "acetic acid derivatives" as defined herein are nonnarcotic analgesics/nonsteroidal antiinflammatory drugs having a free —$CH_2COOH$ group (which optionally can be in the form of a pharmaceutically acceptable salt group, e.g., —$CH_2COO^-Na^+$), typically attached directly to a ring system, preferably to an aromatic or heteroaromatic ring system.

The fenamic acid derivatives which may be used comprise: mefenamic acid, meclofenamic acid, flufenamic acid, niflumic acid, and tolfenamic acid. Structurally related fenamic acid derivatives having similar analgesic and antiinflammatory properties are also intended to be encompassed by this group.

Thus, "fenamic acid derivatives" as defined herein are nonnarcotic analgesics/nonsteroidal antiinflammatory drugs which contain the basic structure:

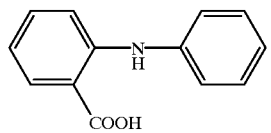

which can bear a variety of substituents and in which the free —COOH group can be in the form of a pharmaceutically acceptable salt group, e.g., —COO⁻Na⁺.

The biphenylcarboxylic acid derivatives which can be used comprise: diflunisal and flufenisal. Structurally related biphenylcarboxylic acid derivatives having similar analgesic and antiinflammatory properties are also intended to be encompassed by this group.

Thus, "biphenylcarboxylic acid derivatives" as defined herein are nonnarcotic analgesics/nonsteroidal antiinflammatory drugs which contain the basic structure:

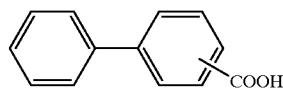

which can bear a variety of substituents and in which the free —COOH group can be in the form of a pharmaceutically acceptable salt group, e.g., —COO⁻Na⁺.

The oxicams which can be used in the present invention comprise: piroxicam, sudoxicam, isoxicam, and 4-hydroxy-1,2-benzothiazine 1,1-dioxide-4-(N-phenyl)-carboxamide. Structurally related oxicams having similar analgesic and antiinflammatory properties are also intended to be encompassed by this group.

Thus, "oxicams" as defined herein are nonnarcotic analgesics/nonsteroidal antiinflammatory drugs which have the general formula:

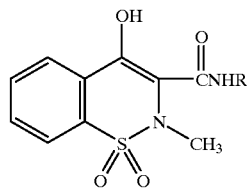

wherein R is an aryl or heteroaryl ring system.

The following NSAIDS may also be used:
acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenfluminzole, fentiazac, feprazone, floctafenine, flunixin, flunoxaprofen, fluproquazone, fopirtoline, fosfosal, furcloprofen, furofenac, glucametacin, guaimesal, ibuproxan, isofezolac, isonixin, isoprofen, isoxepac, isoxicam, lefetamine HCl, leflunomide, lofemizole, lonazolac calcium, lotifazole, loxoprofen, lysin, clonixinate, meclofenamate sodium, meseclazone, microprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenaxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

Finally, NSAIDS which may also be used include the salicylates, especially aspirin, and the phenylbutazones, and pharmaceutically acceptable salts thereof.

The compounds of the present method are known to those skilled in the art and can be synthesized by well known methods. For example, the compounds of the present method where $R_5$ is

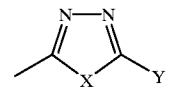

can be synthesized in accordance with U.S. Pat. Nos. 4,962,119; 5,066,668; and 5,212,189;

the disclosures of which are hereby incorporated by reference.

The compounds of the present method where $R_5$ is

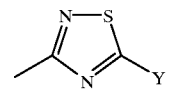

can be synthesized in accordance with U.S. Pat. No. 5,114,958, which is hereby incorporated by reference.

Similarly, the compounds wherein $R_5$ is

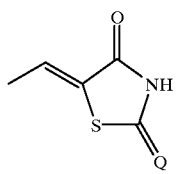

can be synthesized in accordance with U.S. Pat. No. 5,143,929, which is also hereby incorporated by reference.

Preferred compounds to be used in the method of the present invention include the following:

| Compound Number | Name |
| --- | --- |
| 1 | 5-(2-Phenylamino-phenyl)-3H-[1,3,4]oxadiazole-2-thione |
| 2 | 5-(2-Phenylamino-phenyl)-3H-[1,3,4]oxadiazol-2-one |
| 3 | 5-[2-(2,3-Dimethyl-phenylamino)-phenyl]-3H-[1,3,4]oxadiazole-2-thione |
| 4 | 5-[2-(2,6-Dichloro-3-methyl-phenyl-amino)-phenyl]-3H-[1,3,4]oxadiazole-2-thione |
| 5 | 5-[2-(2,6-Dichloro-3-methyl-phenyl-amino)-phenyl]-2,4-dihydro-[1,2,4]triazole-3-thione |
| 6 | 2-[(2,6-dichloro-3-methylphenyl)amino]-,2-(aminothioxomethyl)hydrazide |
| 7 | 3-[2-(2,6-Dichloro-3-methyl-phenyl-amino)-benzylidene]-dihydro-furan-2-thione |

-continued

| Compound Number | Name |
|---|---|
| 8 | 5-[2-(2,6-Dichloro-3-methyl-phenyl-amino)-phenyl]-4-methyl-2,4-dihydro-[1,2,4]triazole-3-thione |
| 9 | 5-[2-(3,5-Di-tert-butyl-4-hydroxy-phenylamino)-phenyl]-3H-[1,3,4]oxadiazole-2-thione |
| 10 | 5-{2-[2-Chloro-3-(1-hydroxy-ethyl)-phenylamino]-phenyl}-3H-[1,3,4]oxadiazole-2-thione |
| 11 | 5-[2-(2,6-Dichloro-3-methyl-phenyl-amino)-benzylidene]-2-thioxo-thiazolidin-4-one |
| 12 | Cyanamide, [5-[2-[(2,6-dichloro-3-methylphenyl)amino]phenyl]-1,3,4-thiadiazol-2-yl]- |
| 13 | Carbamic acid, [1-[2-chloro-3-[[2-(4,5-dihydro-5-thioxo-1,3,4-oxadiazol-2-yl)phenyl]amino]phenyl]ethyl] hydroxy-, ethyl ester |
| 14 | 5-[2-(2,6-Dichloro-3-methyl-phenyl-amino)-benzylidene]-2-imino-thiazolidin-4-one |
| 15 | 5-[2-(2,6-Dichloro-3-methyl-phenyl-amino)-benzylidene]-thiazolidine-2,4-dione |
| 16 | Urea, N-[1-[2-chloro-3-[[(4,5-dihydro-5-thioxo-1,3,4-oxadiazol-2-yl)phenyl]amino]phenyl]ethyl]-N-hydroxy-N'-methyl- |
| 17 | Cyanamide, [5-[[2-[(2,6-dichloro-3-methylphenyl)amino]phenyl]methylene]-4,5-dihydro-4-oxo-2-thiazolyl]-, (Z)- |
| 18 | Cyanamide, [3-[2-[(2,6-dichloro-3-methylphenyi)amino]phenyl]-1,2,4-thiadiazol-5-yl]- |

The examples shown below are intended to illustrate particular embodiments of the invention and are not intended to narrow the scope of the specification, including the claims, in any way.

EXAMPLES

BOVINE NASAL CARTILAGE ASSAY

Background

Interleukin-1 has been shown to induce a loss of proteoglycans from cartilage cultures, possibly by stimulating synthesis of the proteoglycan-degrading enzyme stromelysin and/or other matrix metalloproteinases. The BNC (bovine nasal cartilage) assay provides a model for evaluating chrondroprotective compounds that block cartilage degradation through inhibition of enzyme activity or by altering the gene expression of the matrix metalloproteinases such as stromelysin.

Matrix metalloproteinases (MMPs), including stromelysin, and gelatinase are important enzymes for the degradation of extracellular matrix components such as collagen and proteoglycans in many disease processes including rheumatoid arthritis, osteoarthritis, cancer, periodontitis, and osteoporosis. MMPs are also involved in eye diseases such as corneal ulcer formation and in skin diseases such as chronic ulcers.

Materials

Bovine nasal cartilage is obtained from a local slaughter house (Milan, Mich.); cell culture reagents from Gibco (Grand Island, N.Y.); human recombinant Interleukin-1β (IL-1β) from Boehringer Mannheim (Indianapolis, Ind.); DMB from Polysciences (Warrington, Pa.); Falcon 24 well flat-bottom tissue culture plates from Becton Dickinson (Lincoln Park, N.J.); disposable 20-mL scintillation vials from Kimble Glass (Vinland, N.J.); Papain from Sigma (P-3125, St. Louis, Mo.); high purity dimethyl sulfoxide from Burdic & Jackson (081-1, Distributed by Baxter Healthcare, McGraw Park, Ill.); Sarstedt vials for radioimmune assays (Sarstedt, Newton, N.C.); Sarstedt 96-vial aluminum racks (Sarstedt, Newton, N.C.); Cetus Pro/Pette (Perkin Elmer, Norwalk, Conn.).

Methods

The assay is accomplished in two phases. The cartilage plugs are first incubated with IL-1β in the presence of the compounds of the present method. The amount of proteoglycan released is then quantified by measuring chondroitin sulfate present in the media using the 1,9-Dimethylmethylene Blue Assay (1,9 DMB).

Cartilage Culture

Bovine nasal septum is dissected free of surrounding tissue and wiped with 70% alcohol. A sterile cork borer is used to remove 5-mm cartilage disks of 2- to 3-mm thickness. Explants are equilibrated for 96 hours in F-12 supplemented with 10% fetal calf serum (FCS) and antibiotics at 37° C. in a humidified atmosphere of 95% air and 5% $CO_2$. Explants are then rinsed with 1 mL F-12 Nutrient Mixture (without phenol red) in order to remove traces of FCS. Each treatment group is done in triplicate allowing: controls (500 $\mu$L F-12 medium +110 $\mu$L PBS with 0.1% BSA +7 $\mu$L DMSO); IL-1β (500 $\mu$L F-12 medium without phenol red +100 $\mu$L IL-1β (500 U) +7 $\mu$L DMSO +10 $\mu$L PBS with 0.1% BSA); and dose responses (10, 1, and 0.1 $\mu$M) (F-12 medium without phenol red +100 $\mu$L IL-1β (500 U) +7 $\mu$L compound dissolved in DMSO +10 $\mu$L PBS with 0.1% BSA), to be tested per each 24-well plate. The cartilage plugs are incubated in the presence of conditioned media (IL-1β+compound) for 48 hours. Fresh unconditioned media (no IL-1β or compound) is added and incubated for an additional 24 hours. Both the conditioned and unconditioned media are collected and saved for analysis using the 1,9 DMB assay.

Quantitation of Cartilage Degradation

The ability of a compound to inhibit proteoglycan released from the cartilage plugs is quantified by measuring chondroitin sulfate. This is done using the calorimetric 1,9 DMB assay. Depending on the amount of chondroitin sulfate present in the media a color change will occur turning the normally deep blue dye, vivid pink. This color change is measured using a Titertek Multiscan MCC 340 plate reader at 540 nm. A Cetus Pro/Pette is used to speed dilution and pipetting steps. The Cetus uses Sarstedt vials, designed for radioimmune assays, which have been inserted into Sarstedt 96-vial aluminum racks. The first row of 12 slots is left empty in order to accommodate the chondroitin sulfate standards (0.01–0.32 $\mu$g/mL shark chondroitin sulfate in 0.1 M phosphate buffer, pH 7.0, containing 0.01 M L-cysteine HCl and 0.05 M EDTA). It is necessary to dilute (1:5, 1:10) the medium before a DMF assay is performed by adding 10 $\mu$L of collected media to 290 $\mu$L DMF (16 mg dye/1 L of 0.1 M formate buffer, pH 3.5, containing 5 mL ethanol) and reading at 540 nM. Dilutions are performed on both the 48-hour and 72-hour media samples collected and saved earlier. Once the experiment has been completed, in order to determine the total amount of proteoglycan remaining in the plugs, they are subjected to papain digestion. Cartilage explants are digested in 20-mL glass scintillation vials by adding 50 $\mu$L papain in 1.0 mL cysteine buffer (0.01 M phosphate buffer, pH 7.0 containing 0.01 M L-cysteine HCl and 0.05 M EDTA). Digested material is diluted (1:60) and chondroitin sulfate values determined using the 1,9 DMB assay.

Data Acquisition and Analysis

Absorbance readings from the multi-well plate reader are transferred via the RS232 port to an IBM Personal System/2 Model 60 computer and captured using Lotus Measure (Lotus Development Corporation, Cambridge, Mass.). All statistical analysis of the data is done using Lotus 1-2-3 (Lotus Development Corporation, Cambridge, Mass.).

Determination of chondroitin sulfate in each sample is accomplished by subtracting the constant value determined from the linear regression performed on the standard curve, from the O.D. value for a particular well, and then dividing by the X coefficient calculated from the linear regression done on the standard curve. Each experimental well is split into two samples for determining chondroitin sulfate values, then the two are averaged. This averaged number is multiplied by the total volume, 617 or 500 depending on the time point being assayed, divided by the volume being assayed (10 $\mu$L), and multiplied by the dilution factor (1, 5, 10) to give a total amount of chondroitin sulfate present per experimental well. Once a total value has been determined for each dilution the numbers are compared to find the highest total chondroitin sulfate values ensuring that you have real numbers which are falling on the standard curve. The highest chondroitin sulfate values are transferred to a summary sheet for both the 48-hour and 72-hour media samples. Total chondroitin sulfate present in the cartilage plug after papain digestion is then determined. A 1:60 dilution is generally effective in getting the absorbance readings within the standard curve. Once chondroitin sulfate values have been determined for the plugs they also are transferred to the summary sheet. At this time summary sheet input is complete and release values, as well as inhibition (%), can be calculated. Release is calculated using the formula: (48-hour media +72-hour media)/(48-hour media +72-hour media+digest). Percent inhibition is calculated using the following formula: (((Treatment Release−Control)/(IL-1 Release−Control)) *100).

Table 1 below reports the inhibition activity of representative compounds of the present method. $IC_{50}$ values are the concentration of compound which prevent 50% of proteoglycan loss in the bovine nassal cartilage assay.

TABLE 1

| Compound No. | $IC_{50}$ ($\mu$M) |
|---|---|
| 1 | 0.83 |
| 2 | 40.8 |
| 3 | 31.0 |
| 4 | 26.8 |
| 5 | 9.9 |
| 6 | 1.3 |
| 8 | 4.9 |
| 9 | 23.2 |
| 10 | 18.9 |
| 11 | 1.3 |
| 12 | 6.4 |
| 13 | 5.3 |
| 15 | 4.5 |
| 16 | 1.4 |
| 17 | .8 |
| 18 | .3 |

GELATIN ZYMOGRAPHY

To evaluate the effects of the compounds of the present invention on the expression of 72 kDa and 92 kDa gelatinases, samples obtained from the bovine nasal cartilage study (described above) were subjected to gelatin zymography.

Materials

Mini-PROTEAN II System from Bio-Rad (165-2940, Richmond, Calif.); power supply from Fisher (09-531-50, Pittsburgh, Pa.); gelatin (G2500), Triton X-100 (X-100), Trizma Base (T-1503), sodium azide (S-2002), $CaCl_2$ (C-7902), $ZnCl_2$ (Z-4875), ammonium persulfate (A-6761), lauryl sulfate (SDS; L-3771) were obtained from Sigma Chemical Company (St. Louis, Mo.). Coomassie brilliant blue from ICN (821636, Costa Mesa, Calif.); TEMED from Bio-Rad (161-0801, Richmond, Calif.), bromophenol blue from Fisher (B392, Pittsburgh, Pa.), acetic acid from Fisher (A38S, Pittsburgh, Pa.), methanol from Fisher (A412SK, Pittsburgh, Pa.), and molecular weight standards from Pharmacia (A0446-01, Piscataway, N.J.).

Methods

Gel Preparation

Separating gels (8%) were made by combining 400 $\mu$L gelatin (25 mg/mL) with: 2.5 mL Tris (1.5 M); 100 $\mu$L SDS (10%); 2.6 mL acrylamide (30%); 10 $\mu$L TEMED; 4.6 mL $dH_2O$; 100 $\mu$L ammonium persulfate (10%). Stacking gels (4.5%) were formed by combining: 2.5 mL Tris (0.5 M); 100 $\mu$L SDS (10%); 1.5 mL acrylamide (30%); 10 $\mu$L TEMED; 5.8 mL $dH_2O$; 100 $\mu$L ammonium persulfate (10%).

Sample Preparation and Electrophoresis

Bovine nasal cartilage conditioned media was diluted (1:15) using sample buffer 1X (2% SDS, 15% glycerol, 0.01% bromophenol blue, 0.25M Trizma Base, pH 6.8). Thirty microliters of each of the diluted samples and molecular weight standards were subjected to electrophoresis at 4° C. under constant current conditions (20 mA of current/gel) using Tris/Glycine running buffer (0.5 M Trizma Base, pH 8.8 using glycine, 1% SDS) that was diluted 1:20 before use.

Washing and Incubation

After completion of the electrophoretic procedure, the gel was first washed twice for 15 minutes in 2.5% Triton X-100. The gel was then rinsed with the gel incubation buffer (0.05 M Tris, pH 8.2, 0.005 M $CaCl_2$, 0.5 $\mu$M $ZnCl_2$) and incubated overnight in this buffer at 37° C. After the incubation period, the gel was stained for 30 minutes in 0.125% Coomassie and destained using 10% methanol/5% acetic acid destaining solution.

FIG. 1 is the gelatin zymogram showing the effect of various concentrations of Compound 1 (57081) and Compound 11 (137966) on expression of 72 and 92 kDa gelatinases. As shown in FIG. 1, Compounds 1 and 11 were effective in inhibiting expression of IL-1$\beta$-induced 92 kDa gelatinase in a dose-dependent manner. Interestingly, the compounds had no effect on expression of 72 kDa gelatinase. The lack of effect of the compounds on 72 kDa gelatinase indicates that the effects of Compounds 1 and 11 are specific to 92 kDa and that observed effects are not because of toxicity. It is evident from findings of the present study and from published information that 72 kDa gelatinase is constitutively expressed and that agonists such as IL-1$\beta$ have no effect on expression of this enzyme.

HUMAN ARTICULAR CARTILAGE ASSAY

Materials

Human articular cartilage was obtained from St. Joseph Hospital in Ypsilanti, Mich.; cell culture reagents from Gibco (Grand Island, N.Y.); human recombinant Interleukin-1$\alpha$ (IL1$\alpha$) from Genzyme (Cambridge, Mass.); DMB from Polysciences (Warrington, Pa.); Falcon 24 well flat-bottom tissue culture plates from Becton Dickinson (Lincoln Park, N.Y.); Papain from Sigma (P-3125, St. Louis, Mo.); high purity dimethyl sulfoxide from Burdic & Jackson (081-1, Distributed by Baxter Healthcare, McGraw Park, Ill.); Sarstedt vials for 96-vial aluminum racks (Sarstedt, Newton, N.C.); Cetus Pro/Pette (Perkin Elmer, Norwalk, Conn.); Biomek 1000 (Beckman, Fullerton, Calif.)

Methods

The assay was performed in two phases. The cartilage pieces were first incubated with IL-1α in the presence of compound. The amount of proteoglycan released was then quantified by measuring chondroitin sulfate present in the media using the 1,9-Dimethylmethylene Blue Assay (DMB).

Cartilage Organ Cultures

The articular cartilage used in this study was obtained from osteoarthritis patients undergoing total knee or hip replacment surgery. The ages of the patients ranged from 50 to 70 years. To establish cartilage organ cultures, uniform cartilage slices measuring 11 mm×11 mm were dissected from the underlying bone using a #20 scalpel blade and placed in isotonic saline. The cartilage slices were washed in Gey's balanced salt solution and placed (one piece/well) in Falcon 24 well flat-bottom tissue culture plates (Becton Dickinson, Lincoln Park, N.J.). The cartilage organ cultures were maintained in complete Ham's F-12 (supplemented with 10% fetal calf serum, 6.5 mg/mL Hepes, 58.5 µg/mL glutamine, 200 µg/mL MgSO$_4$, 100 units/mL Pencillin G sodium, 100 µg/mL streptomycin sulfate, and 0.25 µg/mL amphotericin B) at 37° C. in a humidified atmosphere of 95% air and 5% CO$_2$. The cartilage cultures were allowed to equilibrate in this medium for 4 to 5 days. Just before starting the experiment, the serum-containing spent medium was removed and cartilage cultures rinsed with 1 mL F-12 Nutrient Mixture (without phenol red) in order to remove residual FCS. Each treatment group was done in triplicate. The controls received 1 mL F-12 nutrient medium+10 µL PBS with 0.1% BSA+7 µL DMSO, IL-1 treatment group received 1 mL F-12 nutrient +10 µL IL-1α (500 Units) +7 µL DMSO, and the drug treatement group received 1 mL F-12 nutrient medium +10 µL IL-1α (500 Units) +7 µL of the compound dissolved in DMSO. Cartilage pieces were incubated for 7 days with a media change every 48 hours. All the media removed from cultures was collected and analyzed using the 1,9 DMB assay. At the end of experimental period, cartilage pieces were digested with papain and analysed using the 1,9 DMB assay.

Quantitation of Cartilage Degradation

The ability of a compound to inhibit proteoglycan release from cartilage pieces was quantified by measuring chondroitin sulfate. The calorimetric 1,9 DMB assay was used for this purpose. The binding of cationic dye to negatively charged chondroitin sulfate present in the sample results in change in color from blue to pink. This color change was measured using a Titertek Multiscan MCC 340 plate reader at 540 nm. A Cetus Pro/Pette or Biomek 1000 was used to speed dilution and pipetting steps. Both the Cetus and Biomek use Sarstedt Vials, designed for radioimmune assays, which have been inserted into Sarstedt aluminum racks. The first row of 12 tubes was left empty in order to accommodate the chondroitin sulfate standards (0.01–0.32 mg/mL shark chondroitin sulfate in 0.1 M phosphate buffer, pH 7.0, containing 0.01 M L-cysteine HCl and 0.05% M EDTA). It was necessary to dilute (1:5, 1:10) the medium before a DMB assay was performed by adding 10 µL of collected media to 290 µL DMB (16 mg dye/L of 0.1 M formate buffer, pH 3.5, containing 5 mL ethanol) and reading at 540 nm. Dilutions were performed on all media samples collected. Once the experiment was completed the total amount of proteoglycan remaining in the cartilage pieces was determined by digesting cartilage pieces with papain and the digest analyzed using 1,9 DMB assay. Cartilage pieces were digested in 24 well plates by adding 50 µL papain in 1.0 mL cysteine buffer (0.1 M phosphate buffer, pH 7.0 containing 0.01 M L-cysteine HCl and 0.05 M EDTA). Digested material was diluted (1:5, 1:10, 1:20) and chondroitin sulfate values determined using the 1,9 DMB assay.

The inhibitory effect of Compound 1 on IL-1α-induced proteoglycan loss from human osteoarthritic cartilage is shown in Table 2. IL-1α caused a continually increasing level of proteoglycan loss over the time course of the experiment. Compound 1 at a concentration of 30 µM inhibited >70% of IL-1α-induced proteoglycan loss from cartilage, over the course of the experiment. Thus it can be concluded that the compound has chondroprotective value for treatment of arthritis.

TABLE 2

| Treatment | % Proteoglycan Release* | | |
|---|---|---|---|
| | 48 Hours | 96 Hours | 144 Hours |
| Control | 3.7 ± 0.1 | 5.7 ± 0.5 | 7.0 ± 0.7 |
| IL-1α | 9.0 ± 0.3 | 14.4 ± 0.8 | 16.9 ± 2.0 |
| Compound 1 (30 µM) | 4.0 ± 0.2 | 7.4 ± 0.4 | 10.0 ± 0.8 |

*Values are Means (±SE; n = 3)

RABBIT MODEL OF ILL-INDUCED CARTILAGE DEGRADATION

Materials

Rabbits (3.0–3.2 kg) were obtained from Hazelton (Denver, Pa.); Xylazine from W. A. Butler (Columbus, Ohio); Rompun from Miles Inc, (Shawnee Mission, Kans.); Ketamine HCl from Aveco (Fort Dodge Labs, Fort Dodge, Iowa); Pentobarbital from Western Medical Supply (Acadia, Calif.); human recombinant Interleukin-1α (IL-1α) from Genzyme (Cambridge, Mass.); Cetus Pro/Pette (Perkin Elmer, Norwalk, Conn.); Biomek 1000 (Beckman, Fullerton, Calif.).

Methods

The assay was performed in two phases. The hind leg knee joints were first injected with IL-1α and compound for 24 hours. The proteoglycan content of cartilage was then quantified by measuring chondroitin sulfate present using the 1,9-Dimethylmethylene Blue Assay (DMB).

ANIMAL EXPERIMENT

Each treatment was done in quadruplicate, necessitating twelve animals per study. Rabbits were anesthetized by injecting intramuscularly 0.9 mL Rompun combined with 1.8 mL Ketoset. Hind leg knee area was shaved and wiped with 70% EtOH and both drug and IL-1α were injected intra-articulary (27-gauge needle) in succession.

Treatment Groups:
  Control-left knee:
    0.5 mL DMSO/Saline and 2500 U/0.5 mL IL-1α.
  Control-right knee:
    0.5 mL DMSO/Saline and 0.5 mL PBS/0.2% FCS.
  Treatment I-left knee:
    0.5 mL DMSO/Saline containing 8 µg Compound 1 and 2500 U/0.5 mL IL-1α.
  Treatment I-right knee:
    0.5 mL DMSO/Saline containing 8 µg Compound 1 and 0.5 mL PBS/0.2% FCS.
  Treatment II-left knee:
    0.5 mL DMSO/Saline containing 24 µg Compound 1 and 0.5 mL IL-1α.

Treatment II-right knee:
  0.5 mL DMSO/Saline containing 24 µg Compound 1 and 0.5 mL PBS/0.2% FCS.

Animals were sacrificed 24 hours postinjection by first restraining the animals, then injecting 5 mL sodium pentobarbital administered via the ear vein. Joints were lavaged (23-gauge needle) with 1.0 mL of saline. Recovery was considered adequate when ~95% of the volume of saline injected was aspirated. The joint was then opened and the distal end of the femur excised. Approximately 30 mg of cartilage was scraped (#11 scalpel blade) from the femoral condyles.

QUANTITATION OF CARTILAGE DEGRADATION

The ability of a compound to inhibit proteoglycan release from cartilage pieces was quantified by measuring chondroitin sulfate. The calorimetric 1,9 DMB assay was used for this purpose. The amount of chondroitin sulfate present in the media determines a color change, turning a normally deep blue dye to vivid pink. This color change was measured using a Titertek Multiscan MCC 340 plate reader at 540 nm. A Cetus Pro/Pette or Biomek 1000 was used to speed dilution and pipetting steps. Both the Cetus and Biomek use Sarstedt Vials, designed for radioimmune assays, which have been inserted into Sarstedt aluminum racks. The first row of 12 tubes was left empty in order to accommodate the chondroitin sulfate standards (0.01–0.32 µg/mL shark chondroitin sulfate in 0.1 M phosphate buffer, pH 7.0, containing 0.01 M L-cysteine HCl and 0.05% M EDTA). The DMB assay was performed by adding 10 µL of samples to 290 µL DMB (16 mg dye/L of 0.1 M formate buffer, pH 3.5, containing 5 mL ethanol) and reading at 540 nm. Once the experiment was completed the total amount of proteoglycan remaining in the cartilage pieces was determined by digesting cartilage samples with papain and then performing 1,9 DMB assay on the digest. Cartilage pieces were digested in the 24 well plates by adding 50 µL papain in 1.0 mL cysteine buffer (0.1 M phosphate buffer, pH 7.0 containing 0.01 M L-cysteine HCl and 0.05 M EDTA). Digested material was diluted (1:5, 1:10, 1:20) and chondroitin sulfate values determined using the 1,9 DMB assay.

Following are the results from evaluation of Compound 1 in the rabbit model of cartilage degradation. It is evident from results that Compound 1 was effective in inhibiting cartilage degradation in a dose-dependent manner.

| Treatments | Proteoglycan Loss (% Control) |
| --- | --- |
| IL-1α alone | 35.40 ± 3.12 |
| IL-1α + Compound 1 (8 µg/jt) | 18.78 ± 10.98 |
| IL-1α + Compound 1 (24 µg/jt) | 9.35 ± 7.26* |

*Significantly different from animals treated with IL-1α alone (t = 2.90; p = 0.3)

What is claimed is:

1. A method of inhibiting connective tissue degradation, the method comprising administering to a patient having a condition in which connective tissue is degraded a therapeutically effective amount of a compound having the formula

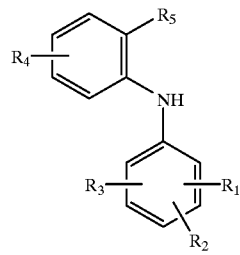

where $R_1$, $R_2$, $R_3$, and $R_4$ are independently hydrogen, hydroxy, halo, amino, nitro, $C_1$–$C_6$ alkyl, $C_3$–$C_6$ cycloalkyl, $C_1$–$C_6$ alkoxy, $CF_3$, CN, $S(O)_n$—[$C_1$–$C_6$ alkyl],

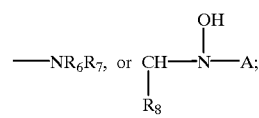

$R_6$ and $R_7$ are independently hydrogen, $C_1$–$C_6$ alkyl or acyl;
n is 0 to 2;
$R_8$ is hydrogen or $C_1$–$C_6$ alkyl;

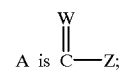

W is S or O;
Z is $C_1$–$C_6$ alkyl, $C_1$–$C_6$ alkoxy, or $NR_9R_{10}$;
$R_9$ and $R_{10}$ are independently hydrogen or $C_1$–$C_6$ alkyl; and
$R_5$ is

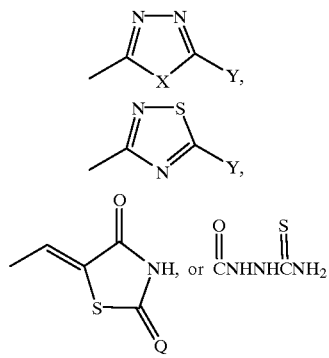

where Y is hydroxy, thiol, amino, or NHCN;
X is sulfur or oxygen; and Q is sulfur, oxygen, NH, or NCN, and the pharmaceutically acceptable salts and prodrugs thereof.

2. The method of claim 1 wherein $R_5$ is

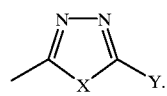

3. The method of claim 2 wherein $R_4$ is hydrogen; $R_1$, $R_2$, and $R_3$ are independently hydrogen, hydroxy, halo, amino, nitro, $C_1$–$C_6$ alkyl, $C_1$–$C_6$ alkoxy, $CF_3$, or CN; and Y is hydroxy, thiol, amino, or NHCN.

4. The method of claim 1 wherein $R_5$ is

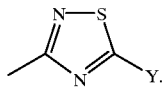

5. The method of claim 4 wherein $R_4$ is hydrogen; $R_1$, $R_2$, and $R_3$ are independently hydrogen, hydroxy, halo, amino, nitro, $C_1$–$C_6$ alkyl, $C_1$–$C_6$ alkoxy, $CF_3$, or CN; and Y is hydroxy, thiol, amino, or NHCN.

6. The method of claim 1 wherein $R_5$ is

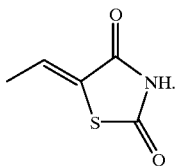

7. The method of claim 6 wherein $R_4$ is hydrogen; $R_1$, $R_2$, and $R_3$ are independently hydrogen, hydroxy, halo, amino, nitro, $C_1$–$C_6$ alkyl, $C_1$–$C_6$ alkoxy, $CF_3$, or CN; and Q is sulfur, oxygen, NH, or NCN.

8. The method of claim 1 wherein $R_5$ is

9. The method of claim 8 wherein $R_4$ is hydrogen; and $R_1$, $R_2$, and $R_3$ are independently hydrogen, hydroxy, halo, amino, nitro, $C_1$–$C_6$ alkyl, $C_1$–$C_6$ alkoxy, $CF_3$, or CN.

10. The method of claim 1 wherein $R_1$ is

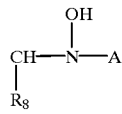

wherein $R_4$ is hydrogen;

$R_2$ and $R_3$ are independently hydrogen, hydroxy, halo, amino, nitro, $C_1$–$C_6$ alkyl, $C_1$–$C_6$ alkoxy, $CF_3$, or CN;

$R_5$ is

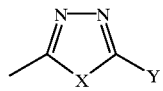

X is sulfur or oxygen; and

Y is hydroxy, thiol, amino, or NHCN.

11. The method of claim 1 wherein the tissue is cartilage.

12. The method of claim 11 wherein the cartilage degradation is the result of a pathological condition or mechanical trauma to the cartilage.

13. The method of claim 1 wherein the tissue is bone.

14. The method of claim 1 wherein the tissue is dermis.

15. The method of claim 1 wherein the tissue is periodontal tissue.

16. The method of claim 1 wherein the tissue is an intervertebral disk.

17. The method of claim 1 wherein the tissue is blood vessel matrix.

18. The method of claim 1 wherein the tissue is neural interstitium.

19. The method of claim 1 wherein the tissue is lung connective tissue.

20. The method of claim 1 wherein the tissue is gastrointestinal connective tissue.

21. The method of claim 1 wherein the tissue is eye connective tissue.

22. A method of inhibiting the production of matrix metalloproteinases, the method comprising administering to a patient having a condition associated with matrix metalloproteinase-mediated tissue degradation a therapeutically effective amount of a compound having the formula

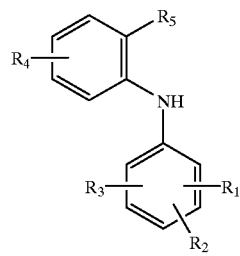

where $R_1$, $R_2$, $R_3$, and $R_4$ are independently hydrogen, hydroxy, halo, amino, nitro, $C_1$–$C_6$ alkyl, $C_3$–$C_6$ cycloalkyl, $C_1$–$C_6$ alkoxy, $CF_3$, CN, $S(O)_n$—[$C_1$–$C_6$ alkyl], $NR_6R_7$, or

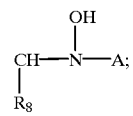

$R_6$ and $R_7$ are independently hydrogen, $C_1$–$C_6$ alkyl, or acyl;

n is 0 to 2;

$R_8$ is hydrogen or $C_1$–$C_6$ alkyl;

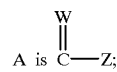

W is S or O;

Z is $C_1$–$C_6$ alkyl, $C_1$–$C_6$ alkoxy, or $NR_9R_{10}$;

$R_9$ and $R_{10}$ are independently hydrogen or $C_1$–$C_6$ alkyl; and $R_5$ is

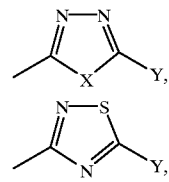

-continued

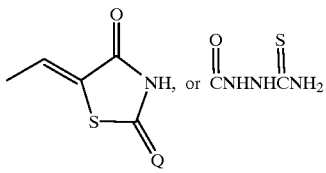

where Y is hydroxy, thiol, amino, or NHCN;

X is sulfur or oxygen; and Q is sulfur, oxygen, NH, or NCN, and the pharmaceutically acceptable salts and prodrugs thereof.

23. The method of claim 22 wherein $R_5$ is

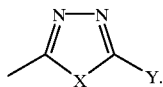

24. The method of claim 23 wherein $R_4$ is hydrogen; $R_1$, $R_2$, and $R_3$ are independently hydrogen, hydroxy, halo, amino, nitro, $C_1$–$C_6$ alkyl, $C_1$–$C_6$ alkoxy, $CF_3$, or CN; and Y is hydroxy, thiol, amino, or NHCN.

25. The method of claim 22 wherein $R_5$ is

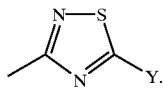

26. The method of claim 25 wherein $R_4$ is hydrogen; $R_1$, $R_2$, and $R_3$ are independently hydrogen, hydroxy, halo, amino, nitro, $C_1$–$C_6$ alkyl, $C_1$–$C_6$ alkoxy, $CF_3$, or CN; and Y is hydroxy, thiol, amino, or NHCN.

27. The method of claim 22 wherein $R_5$ is

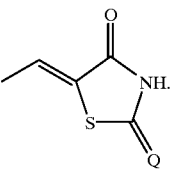

28. The method of claim 27 wherein $R_4$ is hydrogen; $R_1$, $R_2$, and $R_3$ are independently hydrogen, hydroxy, halo, amino, nitro, $C_1$–$C_6$ alkyl, $C_1$–$C_6$ alkoxy, $CF_3$, or CN; and Q is sulfur, oxygen, NH, or NCN.

29. The method of claim 22 wherein $R_5$ is

30. The method of claim 29 wherein $R_4$ is hydrogen; and $R_1$, $R_2$, and $R_3$ are independently hydrogen, hydroxy, halo, amino, nitro, $C_1$–$C_6$ alkyl, $C_1$–$C_6$ alkoxy, $CF_3$, or CN.

31. The method of claim 22 wherein $R_1$ is

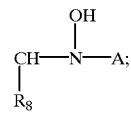

$R_4$ is hydrogen; $R_2$ and $R_3$ are independently hydrogen, hydroxy, halo, amino, nitro, $C_1$–$C_6$ alkyl, $C_1$–$C_6$ alkoxy, $CF_3$, or CN;

$R_5$ is

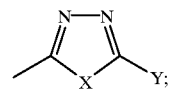

X is sulfur or oxygen; and
Y is hydroxy, thiol, amino, or NHCN.

32. The method of claim 22 wherein the matrix metalloproteinase is 92 kDa gelatinase.

33. The method of claim 22 wherein the condition associated with matrix metalloproteinase-mediated tissue degradation is cancer.

34. The method of claim 22 wherein the condition associated with matrix metalloproteinase-mediated tissue degradation is periodontal disease.

35. The method of claim 22 wherein the condition associated with matrix metalloproteinase-mediated tissue degradation is multiple sclerosis.

36. The method of claim 22 wherein the condition associated with matrix metalloproteinase-mediated tissue degradation is aneurysm formation.

37. The method of claim 22 wherein the condition associated with matrix metalloproteinase-mediated tissue degradation is cutaneous or gastrointestinal ulcer formation.

38. The method of claim 22 wherein the condition associated with matrix metalloproteinase-mediated tissue degradation is emphysema.

39. The method of claim 22 wherein the condition associated with matrix metalloproteinase-mediated tissue degradation is atherosclerosis.

40. The method of claim 22 wherein the condition associated with matrix metalloproteinase-mediated tissue degradation is osteoporosis.

41. The method of claim 22 wherein the condition associated with matrix metalloproteinase-mediated tissue degradation is chronic skin ulcers.

42. The method of claim 22 wherein the condition associated with matrix metalloproteinase-mediated tissue degradation is eye connective tissue ulcers.

43. The method of claim 1 wherein the compound is
   5-(2-Phenylamino-phenyl)-3H-[1,3,4]oxadiazole-2-thione;
   5-(2-Phenylamino-phenyl)-3H-[1,3,4]oxadiazol-2-one;
   5-[2-(2,3-Dimethyl-phenylamino)-phenyl]-3H-[1,3,4]oxadiazole-2-thione;
   5-[2-(2,6-Dichloro-3-methyl-phenylamino)-phenyl]-3H-[1,3,4]oxadiazole-2-thione;
   5-[2-(2,6-Dichloro-3-methyl-phenylamino)-phenyl]-2,4-dihydro-[1,2,4]triazole-3-thione;
   2-[(2,6-dichloro-3-methylphenyl)amino]-, 2-(aminothioxomethyl)hydrazide;
   3-[2-(2,6-Dichloro-3-methyl-phenylamino)-benzylidene]-dihydro-furan-2-thione;

5-[2-(2,6-Dichloro-3-methyl-phenylamino)-phenyl]-4-methyl-2,4-dihydro-[1,2,4]triazole-3-thione;

5-[2-(3,5-Di-tert-butyl-4-hydroxy-phenylamino)-phenyl]-3H-[1,3,4]oxadiazole-2-thione 5-{2-[2-Chloro-3-(1-hydroxy-ethyl)-phenylamino]-phenyl}-3H-[1,3,4]oxadiazole-2-thione;

5-[2-(2,6-Dichloro-3-methyl-phenylamino)-benzylidene]-2-thioxo-thiazolidin-4-one Cyanamide, [5-[2-[(2,6-dichloro-3-methylphenyl)amino]phenyl]-1,3,4-thiadiazol-2-yl]-;

Carbamic acid, [1-[2-chloro-3-[[2-(4,5-dihydro-5-thioxo-1,3,4-oxadiazol-2-yl)phenyl]amino]phenyl]ethyl] hydroxy-, ethyl ester;

5-[2-(2,6-Dichloro-3-methyl-phenylamino)-benzylidene]-2-imino-thiazolidin-4-one;

5-[2-(2,6-Dichloro-3-methyl-phenylamino)-benzylidene]-thiazolidine-2,4-dione;

Urea, N-[1-[2-chloro-3-[[(4,5-dihydro-5-thioxo-1,3,4-oxadiazol-2-yl)phenyl]amino]phenyl]ethyl]-N-hydroxy-N'-methyl-;

Cyanamide, [5-[[2-[(2,6-dichloro-3-methylphenyl)amino]phenyl]methylene]-4,5-dihydro-4-oxo-2-thiazolyl]-, (Z)-; or Cyanamide, [3-[2-[(2,6-dichloro-3-methylphenyl)amino]phenyl]-1,2,4-thiadiazol-5-yl]-.

44. The method of claim 22 wherein the compound is 5-(2-Phenylamino-phenyl)-3H-[1,3,4]oxadiazole-2-thione;

5-(2-Phenylamino-phenyl)-3H-[1,3,4]oxadiazol-2-one;

5-[2-(2,3-Dimethyl-phenylamino)-phenyl]-3H-[1,3,4]oxadiazole-2-thione;

5-[2-(2,6-Dichloro-3-methyl-phenylamino)-phenyl]-3H-[1,3,4]oxadiazole-2-thione;

5-[2-(2,6-Dichloro-3-methyl-phenylamino)-phenyl]-2,4-dihydro-[1,2,4]triazole-3-thione;

2-[(2,6-dichloro-3-methylphenyl)amino]-;

2-(aminothioxomethyl)hydrazide;

3-[2-(2,6-Dichloro-3-methyl-phenylamino)-benzylidene]-dihydro-furan-2-thione;

5-[2-(2,6-Dichloro-3-methyl-phenylamino)-phenyl]-4-methyl-2,4-dihydro-[1,2,4]triazole-3-thione;

5-[2-(3,5-Di-tert-butyl-4-hydroxy-phenylamino)-phenyl]-3H-[1,3,4]oxadiazole-2-thione;

5-{2-[2-Chloro-3-(1-hydroxy-ethyl)-phenylamino]-phenyl}-3H-[1,3,4]oxadiazole-2-thione;

5-[2-(2,6-Dichloro-3-methyl-phenylamino)-benzylidene]-2-thioxo-thiazolidin-4-one;

Cyanamide, [5-[2-[(2,6-dichloro-3-methylphenyl)amino]phenyl]-1,3,4-thiadiazol-2-yl]-;

Carbamic acid, [1-[2-chloro-3-[[2-(4,5-dihydro-5-thioxo-1,3,4-oxadiazol-2-yl)phenyl]amino]phenyl]ethyl] hydroxy-, ethyl ester;

5-[2-(2,6-Dichloro-3-methyl-phenylamino)-benzylidene]-2-imino-thiazolidin-4-one;

5-[2-(2,6-Dichloro-3-methyl-phenylamino)-benzylidene]-thiazolidine-2,4-dione;

Urea, N-[1-[2-chloro-3-[[(4,5-dihydro-5-thioxo-1,3,4-oxadiazol-2-yl)phenyl]amino]phenyl]ethyl]-N-hydroxy-N'-methyl-;

Cyanamide, [5-[[2-[(2,6-dichloro-3-methylphenyl)amino]phenyl]methylene]-4,5-dihydro-4-oxo-2-thiazolyl]-, (Z)-; or Cyanamide, [3-[2-[(2,6-dichloro-3-methylphenyl)amino]phenyl]-1,2,4-thiadiazol-5-yl]-.

\* \* \* \* \*